United States Patent
Wirt et al.

(10) Patent No.: US 6,197,289 B1
(45) Date of Patent: *Mar. 6, 2001

(54) REMOVAL OF BIOLOGICALLY ACTIVE AGENTS

(75) Inventors: David F. Wirt, Prescott, WI (US); Lary M. Sirvio, Cottage Grove, MN (US)

(73) Assignee: Terumo Cardiovascular Systems Corporation, Somerset, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/886,721

(22) Filed: Jul. 1, 1997

(51) Int. Cl.$^7$ ................................................ A61K 47/34
(52) U.S. Cl. ............................................ 424/78.08; 604/5
(58) Field of Search ................................ 422/30, 44, 43; 424/78.08

(56) References Cited

U.S. PATENT DOCUMENTS

| 2,016,962 | 10/1935 | Flint et al. | 260/127 |
| 2,918,462 | 12/1959 | Druey et al. | 260/211 |
| 3,096,602 | 7/1963 | Newmaker, Jr. | 53/22 |

(List continued on next page.)

FOREIGN PATENT DOCUMENTS

| 1160548 | 1/1984 | (CA) . |
| 276 814 A1 | 3/1990 | (DE) . |
| 0 281 128 A1 | 9/1988 | (EP) . |
| 295905B1 | 12/1988 | (EP) . |
| 0466178A1 | 1/1992 | (EP) . |
| 2 041 377 | 9/1980 | (GB) . |
| 88/02623 | 4/1988 | (WO) . |
| 91/16932 | 11/1991 | (WO) . |
| 92/00747 | 1/1992 | (WO) . |
| 92/07023 | 4/1992 | (WO) . |
| 93/02777 | 2/1993 | (WO) . |
| WO93/05793 | 4/1993 | (WO) . |
| WO93/05825 | 4/1993 | (WO) . |
| WO93/10899 | 6/1993 | (WO) . |
| WO 93/14127 | 7/1993 | (WO) . |
| WO96/18423 | 6/1996 | (WO) . |
| WO96/35954A | 11/1996 | (WO) . |
| WO97/07834 | 3/1997 | (WO) . |

OTHER PUBLICATIONS

Bruil, "Poly(ethyleneimine) modified filters for the removal of leukocytes from blood", *J. Bio. Mat. Res.*, 27:1253–68 (1993).

Hou et al., "A Method for Extracorporeal Heparin Removal from Blood by Affinity Chromatography", *Artifical Organs*, 14(6):436–442 (1990).

Hoffman et al., "A New Method for Covalent Coupling of Heparin and Other Glycosaminoglycans to Substances Containing Primary Amino Groups", *Carbohydrate Research*, 117 (1983) pp. 328–331.

Klein, "A Hollow Fiber Device for Direct Absorption of Heparin From Whole Blood", *JASN* 7:9 p. 1410 (1996).

(List continued on next page.)

*Primary Examiner*—Peter F. Kulkosky
(74) *Attorney, Agent, or Firm*—Burns, Doane, Swecker & Mathis, LLP

(57) ABSTRACT

An apparatus for removing a biologically active agent from body fluid that includes an inlet for receiving body fluid, a substrate that includes the reaction product of a substantially water insoluble polymer and a polyalkylene imine, the polyalkylene imine being in a form capable of binding a biologically active agent in the body fluid, and an outlet through which the body fluid flows following contact with the substrate.

10 Claims, 2 Drawing Sheets

U.S. PATENT DOCUMENTS

| | | | |
|---|---|---|---|
| 3,453,194 | 7/1969 | Bennett et al. | 284/159.12 |
| 3,475,358 | 10/1969 | Bixler et al. | 260/17.4 |
| 3,475,410 | 10/1969 | Britton | 260/212 |
| 3,616,935 | 11/1971 | Love et al. | 210/500 |
| 3,617,344 | 11/1971 | Leininger et al. | 117/47 |
| 3,634,123 | 1/1972 | Eriksson et al. | 117/47 |
| 3,639,141 | 2/1972 | Dyck | 117/47 |
| 3,673,612 | 7/1972 | Merrill et al. | 3/1 |
| 3,755,218 | 8/1973 | Yen et al. | 260/9 |
| 3,766,104 | 10/1973 | Bonin et al. | 260/9 |
| 3,796,634 | 3/1974 | Haynes et al. | 195/63 |
| 3,810,781 | 5/1974 | Eriksson et al. | 117/47 |
| 3,826,678 | 7/1974 | Hoffman et al. | 117/81 |
| 3,846,353 | 11/1974 | Grotta | 260/9 |
| 3,853,804 | 12/1974 | Yen et al. | 260/32.6 |
| 3,947,352 | 3/1976 | Cuatrecasas et al. | 210/31 |
| 4,001,583 | 1/1977 | Barrett | 250/303 |
| 4,046,725 | 9/1977 | Pusineri | 260/9 |
| 4,048,064 | 9/1977 | Clark, III | 210/23 |
| 4,085,019 | 4/1978 | Green | 204/159.23 |
| 4,102,746 | 7/1978 | Goldberg | 195/63 |
| 4,116,898 | 9/1978 | Dudley et al. | 260/17.4 |
| 4,118,485 | 10/1978 | Eriksson et al. | 424/183 |
| 4,141,857 | 2/1979 | Levy et al. | 502/439 |
| 4,217,338 | 8/1980 | Quash | 424/1 |
| 4,229,838 | 10/1980 | Mano | 3/1.4 |
| 4,239,664 | 12/1980 | Teng et al. | 260/17.4 |
| 4,265,827 | 5/1981 | Sabacky | 260/440 |
| 4,265,927 | 5/1981 | Ericksson et al. | 427/2 |
| 4,268,423 | 5/1981 | Rohrbach et al. | 252/430 |
| 4,301,067 | 11/1981 | Koshugi | 260/112.5 |
| 4,326,532 | 4/1982 | Hammar | 128/349 |
| 4,329,383 | 5/1982 | Joh | 428/36 |
| 4,331,697 | 5/1982 | Kudo et al. | 427/2 |
| 4,349,467 | 9/1982 | Williams et al. | 525/54.2 |
| 4,350,806 | 9/1982 | Wagener | 528/289 |
| 4,369,256 | 1/1993 | Casu et al. | 521/25 |
| 4,424,346 | 1/1984 | Hall et al. | 536/20 |
| 4,521,564 | 6/1985 | Solomon et al. | 525/54.1 |
| 4,526,714 | 7/1985 | Feijen et al. | 260/112 |
| 4,565,740 | 1/1986 | Golander et al. | 428/409 |
| 4,600,652 | 7/1986 | Solomon et al. | 428/423.3 |
| 4,613,517 | 9/1986 | Williams et al. | 427/2 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,737,544 | 4/1988 | McCain et al. | 525/54.1 |
| 4,786,556 | 11/1988 | Hu et al. | 428/412 |
| 4,800,016 | 1/1989 | Yang | 210/206 |
| 4,806,595 | 2/1989 | Noishiki et al. | 525/54.2 |
| 4,810,784 | 3/1989 | Larm | 536/20 |
| 4,863,611 | 9/1989 | Bernstein et al. | 210/661 |
| 4,865,870 | 9/1989 | Hu et al. | 427/2 |
| 4,871,357 | 10/1989 | Hsu et al. | 604/266 |
| 4,876,126 | 10/1989 | Takemura et al. | 428/35.7 |
| 4,935,204 | 6/1990 | Seidel et al. | 424/101 |
| 4,944,767 | 7/1990 | Barbucci et al. | 623/66 |
| 4,987,181 | 1/1991 | Bichon et al. | 525/54.1 |
| 5,000,854 | 3/1991 | Yang | 210/638 |
| 5,013,717 | 5/1991 | Solomon et al. | 514/56 |
| 5,047,020 | 9/1991 | Hsu | 604/266 |
| 5,049,403 | 9/1991 | Larm et al. | 427/2 |
| 5,053,048 | 10/1991 | Pinchuk | 623/1 |
| 5,061,750 | 10/1991 | Feijen et al. | 525/54.1 |
| 5,116,962 | 5/1992 | Stuber et al. | 525/54.2 |
| 5,132,108 | 7/1992 | Narayanan et al. | 424/78.17 |
| 5,145,956 | 9/1992 | Lam et al. | 536/124 |
| 5,151,192 | 9/1992 | Matkovich et al. | 210/646 |
| 5,159,050 | 10/1992 | Onwumere | 528/67 |
| 5,165,919 | 11/1992 | Sasaki et al. | 424/488 |
| 5,182,317 | 1/1993 | Winters et al. | 523/112 |
| 5,198,493 | 3/1993 | Holmberg et al. | 525/54.1 |
| 5,211,850 | 5/1993 | Shettigar et al. | 210/645 |
| 5,213,898 | 5/1993 | Larm et al. | 428/422 |
| 5,217,492 | 6/1993 | Guire et al. | 623/11 |
| 5,219,926 | 6/1993 | Lindman et al. | 525/54.1 |
| 5,240,994 | * 8/1993 | Brink et al. | 525/54.2 |
| 5,250,613 | 10/1993 | Bergstrom et al. | 525/54.1 |
| 5,258,041 | 11/1993 | Guire et al. | 623/66 |
| 5,308,641 | * 5/1994 | Cahalan et al. | 427/228 |
| 5,350,800 | 9/1994 | Verhoeven et al. | 525/54.2 |
| 5,391,580 | 2/1995 | Douglas et al. | 521/27 |
| 5,415,938 | 5/1995 | Cahalan et al. | 428/409 |
| 5,416,198 | 5/1995 | Anderson et al. | 536/111 |
| 5,476,715 | 12/1995 | Otto | 428/407 |
| 5,532,311 | 7/1996 | Sirvio et al. | 525/54.2 |
| 5,607,475 | 3/1997 | Cahalan et al. | 623/11 |

OTHER PUBLICATIONS

Larm et al., "An Approach to Antithrombosis by Surface Modification", *Progress in Artifical Organs*, pp. 313–318 (1985).

Larm et al., "A New Non–Thrombogenic Surface Prepared by Selective Covalent Binding of Heparin Via A Modified Reducing Teminal Residue", (1984).

Ma et al., "Interaction of Heparin with Polyallylamine–Immobilized Surfaces," *J. Biom. Mat. Res.*, 27:357–365 (1993).

Marchisio et al., "Novel Approach To The Problems of Heparin In Hemodialysis: The Use of A Deheparinizing Filter," *Polymers In Med. III*, pp. 111–117 and 120 (1988) (pp. 118–119 are missing).

Matthey et al., "A Selective De–Heparinizer Filter Made of New Cross–Linked Polymers of a Poly–Amido–Amine Structure," *Experientia*, 29: 93–95 (1973).

Wenz et al., "Rapid Removal of Heparin from Plasma by Affinity Filtration," *Coagulation and Transf. Med.*, 93:3, pp. 385–390 (1991).

Tao et al., "Extracorporeal Heparin Removal Following Cardiopulmonary Bypass with a Heparin Removal Device: An Alternative to Protamine," *Crit. Care Med.*, 25:1 (Suppl.) (1997).

* cited by examiner

REMOVAL OF BIOLOGICALLY ACTIVE AGENTS

BACKGROUND OF THE INVENTION

The invention relates to removing biologically active agents from liquids.

At times it is necessary to remove biologically active agents from liquids such as body fluids. Heparin, for example, is routinely added to blood as an anticoagulant in applications where the blood is to be transferred through extracorporeal circuits such as those employed in hemodialysis and cardiovascular surgery. The presence of heparin in the blood, however, creates a significant risk of hemorrhaging. Thus, it is highly desirable to remove excess heparin from blood when it is no longer desirable for the blood to have anticoagulating properties.

SUMMARY OF THE INVENTION

In one aspect, the invention features an apparatus for removing a biologically active agent (e.g., heparin) from body fluid that includes an inlet for receiving body fluid, a substrate that includes the reaction product of a substantially water insoluble polymer and a polyalkylene imine, the polyalkylene imine being in a form capable of binding a biologically active agent in the body fluid, and an outlet through which the body fluid flows following contact with the substrate. The invention also features a method for removing a biologically active agent from body fluid using this apparatus.

Biologically active agents which can be removed include negatively charged materials. Specific examples of biologically active agents that can be removed include heparin, heparan sulfate, hyaluronic acid, dermatan sulfate, chitosan, derivatives thereof, and combinations thereof.

The preferred polyalkylene imine is polyethylene imine. Preferred substantially water insoluble polymers include functional groups such as ester groups that are capable of forming a covalent bond with the polyalkylene imine. Specific examples include (a) the reaction product of an alkyl acrylate and an alkyl methacrylate, b) the reaction product of an alkyl acrylate, an alkyl methacrylate, and a hydroxy alkyl acrylate, and (c) the reaction product of an alkyl methacrylate, an alkyl acrylate, and N-vinyl pyrrolidone (e.g., the reaction product of methyl methacrylate, isooctyl acrylate, and N-vinyl pyrrolidone). The acrylate, methacrylate, and N-vinyl pyrrolidone may be provided in the form of monomers, oligomers, or a combination thereof.

In one preferred embodiment, the apparatus further includes a conduit for transporting body fluid from a patient to the inlet and a conduit for transporting body fluid through the outlet to a patient. In one embodiment, the apparatus is in fluid communication with a blood oxygenator. In another embodiment, the apparatus is in fluid communication with a blood dialyzer. The apparatus may also be in the form of a syringe.

In a second aspect, the invention features an apparatus for removing a biologically active agent from body fluid that includes an inlet for receiving body fluid, a substrate that includes a polyalkylene imine immobilized thereon in a form capable of binding the biologically active agent, and an outlet through which the body fluid flows following contact with the substrate. The invention also features a method for removing a biologically active agent from body fluid using this apparatus.

Throughout this application the following definitions apply:

A "biologically active agent" is a material that, when in contact with a patient's blood, plasma, or other body fluids or tissues under physiological conditions, exhibits biological activity. For instance, a material such as heparin is "biologically active" in the sense that it acts as an anti-coagulant in the presence of blood.

The invention provides a simple and effective means for removing biologically active agents such as heparin from body fluid. The process may be conducted in the presence of red blood cells.

Other features and advantages of the invention will be apparent from the following description of the preferred embodiments thereof, and from the claims.

DESCRIPTION OF THE PREFERRED EMBODIMENTS

Figure 1:
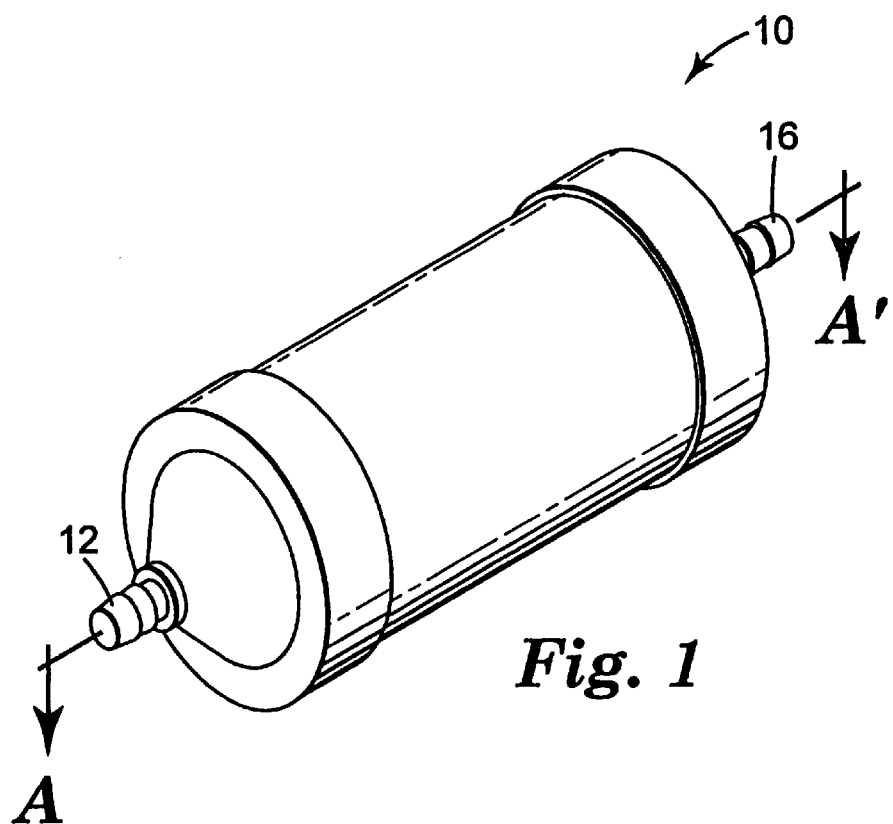
FIG. 1 is a perspective view of an apparatus for removing a biologically active agent according to one embodiment of the invention.
Figure 2:
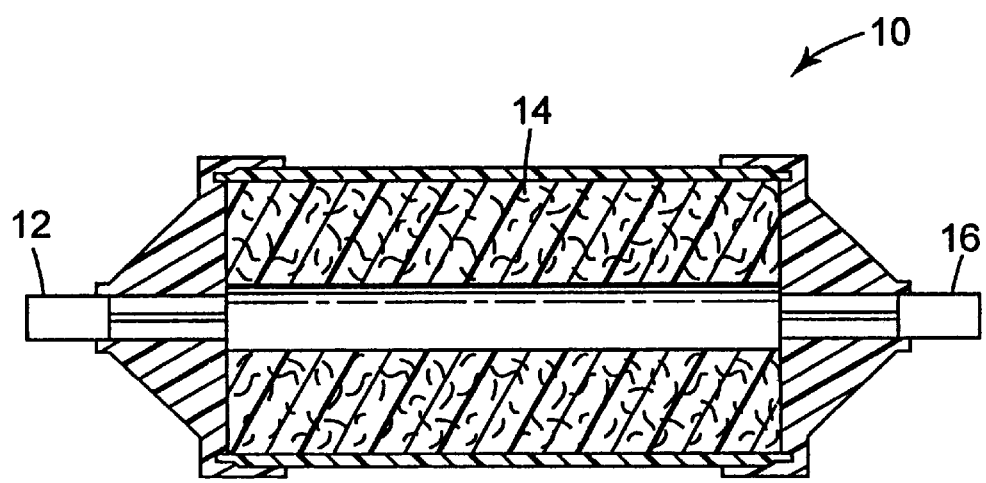
FIG. 2 is a cross-sectional view taken along line A–A' of the apparatus shown in FIG. 1.
Figure 3:
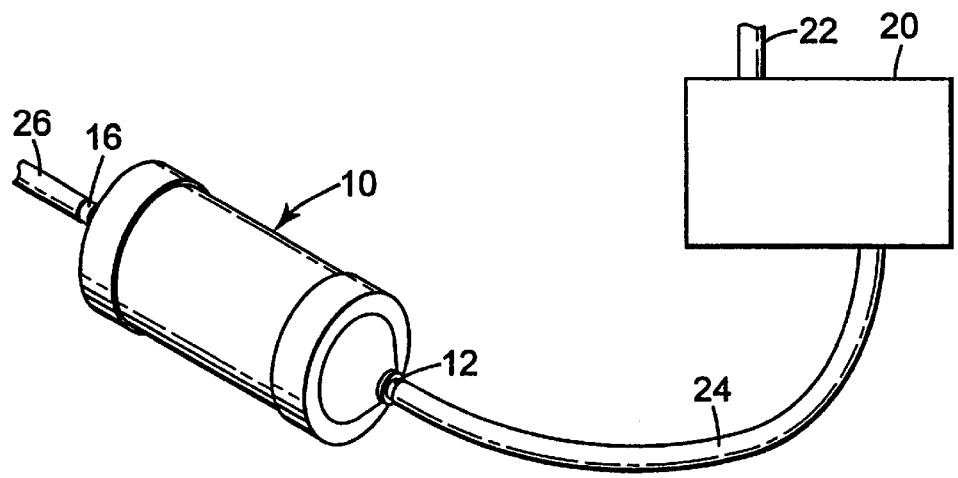
FIG. 3 is a schematic view of the apparatus of FIG. 1 in fluid communication with an oxygenator.

Referring to FIGS. 1 and 2, there is shown an apparatus 10 for removing a biologically active agent, e.g., heparin, from body fluid featuring an inlet 12 for receiving a body fluid, a substrate 14, and an outlet 16 through which the body fluid flows following contact with substrate 14. Inlet 12 coupled to oxygenator 20 by tubing 24 is shown in FIG. 3. A pump (not shown) may be used to facilitate the flow of body fluid from oxygenator 20 to inlet 12. Outlet 16 is coupled to a patient by tubing 26.

Figure 4:
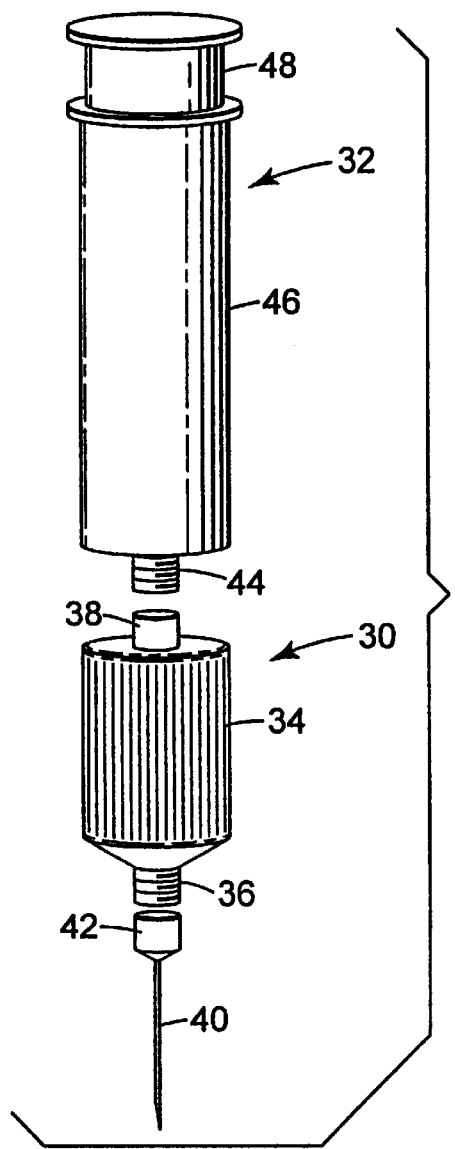
FIG. 4 is a perspective view of an apparatus for removing a biologically active agent according to a second embodiment of the invention.

Referring to FIG. 4, an apparatus 30 for removing a biologically active agent is shown in the form of a syringe. The apparatus 30 includes an inlet 36 for receiving a body fluid, a substrate 34, and an outlet 38 through which body fluid flows following contact with substrate 34. Inlet 36 is connected to needle 40 by a connecting portion 42. Outlet 38 is connected to cylinder 46 by connecting portion 44.

Substrates 14 and 34 include a polyalkylene imine immobilized thereon in a form that is capable of binding a biologically active agent present in a body fluid.

The biologically active agent preferably includes negatively charged groups. It may be an anti-thrombotic agent (e.g., a glycosaminoglycan (or a derivative thereof) such as heparin or a heparin derivative), an anti-microbial agent, a therapeutic agent (e.g., drug or growth factor), an enzyme, or a cell attachment protein. Other examples of suitable biologically active agents include heparan sulfate, hyaluronic acid, dermatan sulfate, chitosan, and derivatives thereof. More than one agent can be removed from body fluid.

Suitable polyalkylene imines are those having an average molecular weight of between about 300 and 1,000,000. One example of a suitable polyalkylene imine is polyethylene imine having an average molecular weight of 750,000, available from the Aldrich Chemical Co., Milwaukee, Wis.

The polyalkylene imine may be immobilized on a variety of substrates. Generally, any substrate on which polyethylene imine can be immobilized and which can pass a body fluid (e.g., blood or plasma) can be used. Examples of suitable substrates include woven fabrics, non-woven materials, foams, films, porous membranes, porous fibers, porous ceramics, metals, polymers, and beads. Specific examples of suitable polymer substrates include polypropylene, poly (vinyl chloride), poly (methyl methacrylate), polytetrafluoroethylene, polysulfone, polyethylene terephthalate, polycarbonate, polyethylene, polystyrene, and polyurethane. The substrate may take many forms, e.g., a cylindrical roll of woven fabric wound around a central mandrel and placed in an housing.

A variety of processes may be used to immobilize the polyalkylene imine onto the surface of the substrate. One such process involves contacting the substrate with a polyalkylene imine, which will render the surface wettable and positively charged. The polyalkylene imine is preferably in the form of an aqueous solution, e.g., a 0.1% by weight solution of polyalkylene imine in water, when it is contacted with the substrate.

The polyalkylene imine is then contacted with a polymeric anionic compound, thereby further increasing the wettability of the surface. The polymeric anionic compound is contacted with the polyalkylene imine in the form of a solution that includes, e.g., 0.03% by weight polymeric anionic compound (e.g., dextran sulfate) in a citrate buffer (pH =3.9). Examples of other suitable polymeric anionic compounds include polygalacturonic acid and polyacrylic acid.

The use of a polymeric anionic compound also allows the addition of a second polyalkylene imine (which may be the same as, or different from, the first polyalkylene imine) to the surface. The second polyalkylene imine binds to the polymeric anionic compound. At this point the surface has been sequentially treated with three agents to create a primed surface: (1) first polyalkylene imine, (2) polymeric anionic compound, and (3) second polyalkylene imine. The sequence may be repeated as many times as necessary, the particular number of steps being selected by the particular application for which the treated article is intended. This process is further described in U.S. Pat. No. 5,532,311 (Sirvio et al.), incorporated herein by reference.

A second process for preparing a substrate having polyalkylene imine immobilized thereon involves coating the substrate with a priming solution that contains an organic solvent and the reaction product of a polyalkylene imine, such as polyethylene imine, and a water insoluble polymer, and then drying the substrate. The resulting primed surface of the substrate is coated with the reaction product of the polyalkylene imine and the water insoluble polymer. The solution may be coated on the substrate and dried as many times as is necessary to achieve the desired concentration of polyalkylene imine on the substrate. The particular amount of coating and concentration of polyalkylene imine on the substrate will depend upon the particular application for which the treated substrate is intended. This process is also described in co-pending, commonly assigned U.S. patent application Ser. No. 08/886,720 entitled "Process For Modifying Surfaces Using The Reaction Product Of A Polyalkylene Imine And A Substantially Water-Insoluble Polymer," filed concurrently with the present application and incorporated herein by reference.

Preferred polyalkylene imine priming solutions include between about 0.1 to about 20% solids in a solution that includes between about 50 and about 99.9% organic solvent and up to about 50% water. The weight to weight ratio of substantially water insoluble polymer to polyalkylene imine is preferably in the range of between about 0.1:1 and about 10:1, more preferably about 4:1.

Preferred substantially water insoluble polymers are those polymers that provide functional groups, e.g., ester groups, capable of forming a covalent bond with the amine groups of the polyalkylene imine while not interfering with the ability of the polyalkylene imine to bind to a biologically active agent. The substantially water insoluble polymer preferably is soluble in those organic solvents in which the polyalkylene imine is soluble.

Suitable substantially water insoluble polymers include water insoluble acrylate-containing polymers such as, e.g., alkyl acrylate-alkyl methacrylate copolymers (e.g., copolymers of isooctyl acrylate and methyl methacrylate), alkyl methacrylate-alkyl acrylate-N-vinyl pyrrolidone terpolymers (e.g., methyl methacrylate-isooctyl acrylate-N-vinyl pyrrolidone), and alkyl acrylate-alkyl methacrylate-hydroxyalkyl methacrylate terpolymers (e.g., isooctyl acrylatemethyl methacrylate-hydroxypropyl methacrylate).

Examples of alkyl methacrylate-alkyl-acrylate-N-vinyl pyrrolidone terpolymers and their methods of manufacture are described in U.S. Pat. No. 4,584,192 (Dell), incorporated herein by reference.

Preferred organic solvents are those capable of dissolving the polymer and rapidly evaporating after the application of the priming solution to the substrate surface. Suitable organic solvents include alkyl alcohols such as, e.g., methanol, ethanol, and isopropyl alcohol.

Another process for preparing a substrate having polyalkylene imine immobilized thereon involves contacting the substrate with a dilute solution of high molecular weight polyalkylene imine and a low concentration of glutaraldehyde, e.g., an aqueous solution of between about 0.01 and about 0.5% by weight polyethylene imine and between about 0.0001 and about 0.5% by weight glutaraldehyde, optionally followed by contact again with polyalkylene imine, e.g., an aqueous solution of between about 0.01 and about 0.5% by weight polyethylene imine. This process is also described in co-pending commonly assigned U.S. patent Ser. No. 08/886,752, abandoned, entitled "Process For Modifying Surfaces Using Glutaraldehyde And A Polyalkylene Imine," filed concurrently with the present application and incorporated herein by reference.

The apparatus for removing a biologically active agent may be used in conjunction with other devices. Referring to FIGS. 1–3, the apparatus 10 for removing a biologically active agent is shown in series with an oxygenator 20. Blood flows from the patient to oxygenator 20 via tubing 22 where the blood undergoes oxygenation. The blood then flows to inlet 12 of apparatus 10 for removing a biologically active agent via tubing 24 with the aid of a pump (not shown). As blood flows through substrate 14 the biologically active agent present in the blood binds with the polyalkylene imine. The blood (minus the bound biologically active agent) flowing through outlet 16 is then returned to the patient via tubing 26.

Alternatively, referring to FIG. 4, the apparatus for removing a biologically active agent 30 is in the form of a syringe. Needle 40 is inserted into a patient so as to contact a supply of blood. Plunger 48 is then pulled so as to create a vacuum, which draws blood from the patient, through needle 40, through substrate 34, and into cylinder 46. As the blood passes over the surface of the substrate 34, a biologically active agent present in the blood binds with the polyethylene imine present on the substrate 34. The blood collected in cylinder 46 may then be analyzed. The apparatus may also be used to remove a biologically active agent from previously drawn blood.

Although not shown, the apparatus for removing a biologically active agent may also be coupled to a variety of extracorporeal circuits.

The invention will now be further described by way of the following example.

EXAMPLE 1

A heparin removal device was prepared using a substrate measuring 2.67 square meters made of precision woven fabric. The fabric was woven in a plain weave from 100 micron diameter polyester fiber. It featured 200 micron mesh openings and a 43% open area (Saati PES 200/43). The fabric substrate was continuously coated and dried on a web-coating machine using a coating solution containing 2.5% by weight polymer, 15% by weight water, and 82.5% by weight isopropanol.

The polymer was the reaction product of polyethylene imine (PEI) and an isooctyl acrylatemethyl methacrylate-N-vinyl pyrrolidone terpolymer in which the weight to weight ratios of the respective monomers was 50:40:10. The weight to weight ratio of PEI to polymer was 4:1. The polymer was prepared as follows.

Isooctyl acrylate, methyl methacrylate, and N-vinyl pyrollidone monomers were polymerized as described in Examples 2–8, formulation D of U.S. Pat. No. 4,584,192, to form a terpolymer. The terpolymer was then repeatedly washed and distilled to remove any acetone. Once the acetone was removed, the terpolymer was placed in isopropyl alcohol.

The terpolymer solution and polyethylene imine were then placed in a solution of isopropyl alcohol and water. The resulting solution contained 4:1 polyethylene imine/terpolymer as a 2.5% by weight solids solution in 82.5% by weight isopropyl alcohol and 15% by weight water.

The coated fabric was wound onto a mandrel to form a 2.5 inch diameter roll and inserted into a tubular acrylic housing with fittings on both ends for ⅜ inch tubing. The device was then tested for its ability to remove heparin from the blood of a 66 kg anesthetized swine.

The swine was systemically heparinized to maintain an ACT greater than 400 seconds and was placed on a cardiopulmonary bypass (CPB) at normothermic conditions for 60 minutes. The swine was then removed from CPB and its blood was shunted through the heparin removal device from the aorta to the right atrium at a flow rate of approximately 1 liter/minute. The blood entered the device at one end, flowed axially through the coated fabric roll, and exited through the opposite end. Hemodynamic, hematological, and clinical chemistry parameters were measured pre-CPB, post-CPB, and after connection of the device for 5, 10, 15, 20, and 30 minutes. The heparin removal device reduced the circulating heparin from 2.0 IU/ml to 0.21 IU/ml in 10 minutes. Hemodynamic, hematological, and clinical chemistry measurements were not affected or were within acceptable limits following the heparin removal procedure.

Other embodiments are within the following claims.

What is claimed is:

1. A method for removing a biologically active agent from body fluid comprising:

contacting body fluid with a substrate comprising the reaction product of a substantially water insoluble polymer and a polyalkylene imine, said polyalkylene imine in a form capable of binding said biologically active agent in said body fluid and said substantially water insoluble polymer comprising ester functional groups capable of forming a covalent bond with said propyalkylene imine, wherein said substrate is formed by coating a surface with a solution comprising said reaction product.

2. The method of claim 1, wherein said biologically active agent comprises a negatively charged material.

3. The method of claim 1, wherein said biologically active agent is heparin.

4. The method of claim 1, wherein said biologically active agent is selected from the group consisting of heparan sulfate, hyaluronic acid, dermatan sulfate, chitosan, derivatives thereof, and combinations thereof.

5. The method of claim 1, wherein said polyalkylene imine comprises polyethylene imine.

6. The method of claim 1, wherein said substantially water insoluble polymer comprises the reaction product of an alkyl methacrylate and an alkyl acrylate.

7. The method of claim 1, wherein said substantially water insoluble polymer comprises the reaction product of an alkyl methacrylate, an alkyl acrylate, and a hydroxy alkyl methacrylate.

8. The method of claim 1, wherein said substantially water insoluble polymer comprises the reaction product of an alkyl methacrylate, an alkyl acrylate, and N-vinyl pyrrolidone.

9. The method of claim 1, wherein said substantially water insoluble polymer comprises the reaction product of methyl methacrylate, isooctyl acrylate, and N-vinyl pyrrolidone.

10. The method of claim 1, wherein the substantially water insoluble polymer forms a covalent bond with the polyalkylene imine in the reaction product.

* * * * *